(12) United States Patent
Montgomery

(10) Patent No.: US 7,087,042 B2
(45) Date of Patent: Aug. 8, 2006

(54) OSTOMY APPLIANCE AND METHOD OF USE

(76) Inventor: Robert Montgomery, 1685 W. 12th St., Reno, NV (US) 89503

( * ) Notice: Subject to any disclaimer, the term of this patent is extended or adjusted under 35 U.S.C. 154(b) by 0 days.

(21) Appl. No.: 10/956,787

(22) Filed: Oct. 1, 2004

(65) Prior Publication Data

US 2006/0074389 A1    Apr. 6, 2006

(51) Int. Cl.
*A61F 5/44* (2006.01)
*A61M 31/00* (2006.01)

(52) U.S. Cl. .................. 604/342; 604/277; 604/344; 604/355

(58) Field of Classification Search ............ 604/277, 604/322–345, 355
See application file for complete search history.

(56) References Cited

U.S. PATENT DOCUMENTS

| | | | | |
|---|---|---|---|---|
| 2,441,508 A | * | 5/1948 | Porcell | 604/340 |
| 2,639,710 A | * | 5/1953 | Fazio | 604/342 |
| 3,736,934 A | * | 6/1973 | Hennessy | 604/342 |
| 4,726,354 A | * | 2/1988 | Fujita | 600/32 |
| 4,846,798 A | * | 7/1989 | Holtermann et al. | 604/339 |
| 5,098,420 A | * | 3/1992 | Iacone | 604/338 |
| 5,209,744 A | * | 5/1993 | Abe et al. | 604/342 |
| 5,312,381 A | * | 5/1994 | Brooks | 604/338 |
| 5,501,677 A | * | 3/1996 | Jensen | 604/338 |
| 5,785,695 A | * | 7/1998 | Sato et al. | 604/339 |
| 5,865,819 A | * | 2/1999 | Cisko et al. | 604/339 |
| 6,520,943 B1 | * | 2/2003 | Wagner | 604/338 |
| 6,582,410 B1 | * | 6/2003 | Rutman | 604/335 |
| 6,679,866 B1 | * | 1/2004 | Gunawan | 604/338 |
| 6,830,565 B1 | * | 12/2004 | Cisko, Jr. | 604/336 |

FOREIGN PATENT DOCUMENTS

GB    2 196 257 A    *    4/1988
WO    WO 01/35875 A2    *    5/2001

* cited by examiner

*Primary Examiner*—Tatyana Zalukaeva
*Assistant Examiner*—Michael G. Bogart

(57) ABSTRACT

A new and improved ostomy or incontinence appliance that is user-friendly, sanitary, environmentally safe, provides novel attachment means, and further includes optional features including a temporary breather flange that allows for healing of the stoma orifice when irritated and a novel stoma locator adaptor that aids a user and provides proper placement and alignment of the appliance.

19 Claims, 3 Drawing Sheets

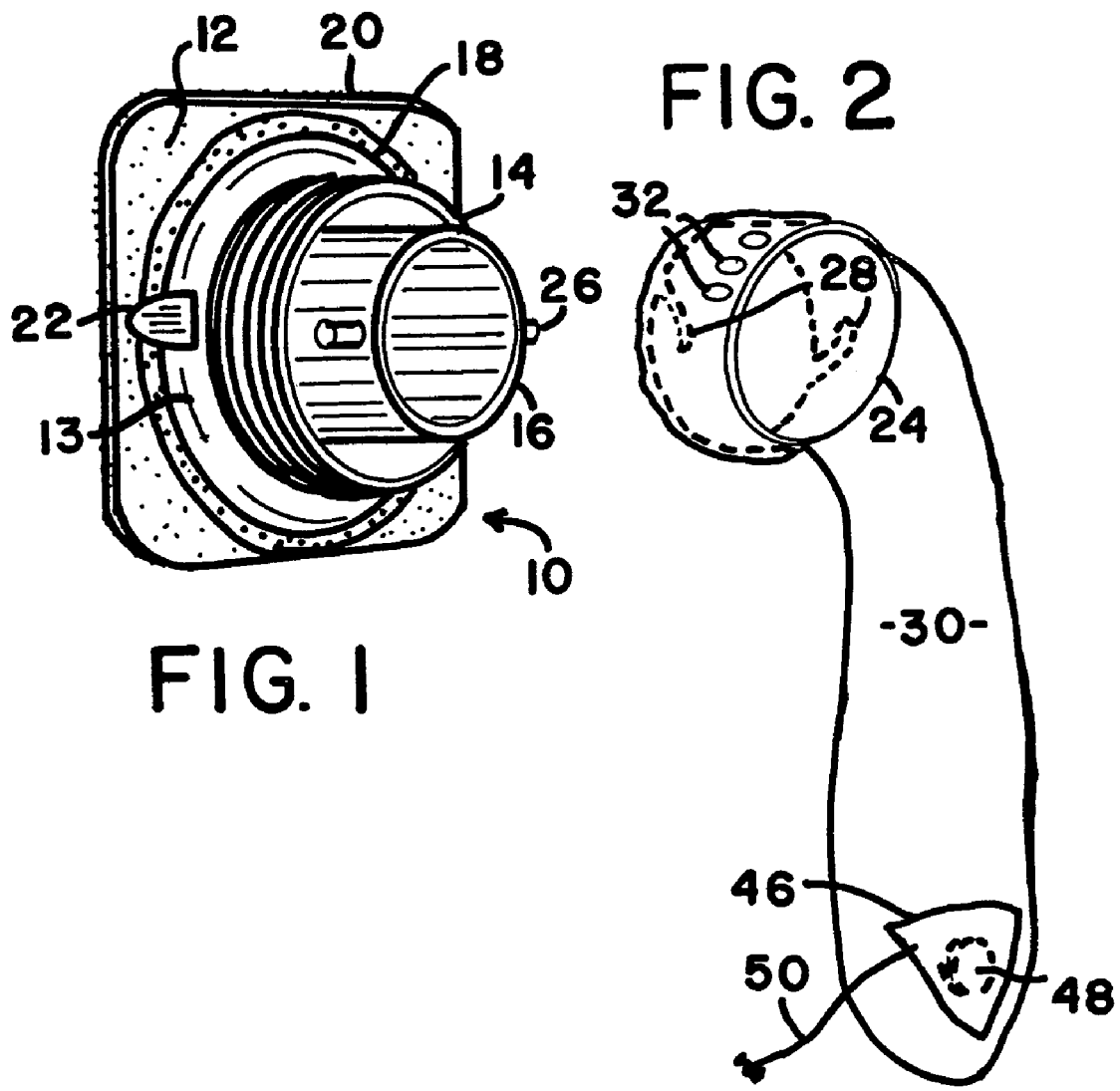

OSTOMY APPLIANCE AND METHOD OF USE

FIELD OF THE INVENTION

The present invention in general relates to ostomy bags and the like but more particularly pertains to an improved ostomy appliance that is user-friendly, sanitary, environmentally safe, and further includes novel improved attachment means heretofore not taught. Additionally, the appliance provides optional features including a temporary breather flange that allows for healing of the stoma orifice when irritated or infected and a novel stoma locator adaptor that aids a user and provides proper placement and alignment of the appliance.

BACKGROUND OF THE INVENTION

One of the problems associated with ostomy care is the disposal of the ostomy collection pouch after it has been used. If the used pouch is disposed of by flushing down a toilet, there is a risk that the pouch may become trapped in a toilet passage or sewer line, thereby causing plumbing problems. Thus some users empty the contents of the pouch into the toilet and then discard the pouch in the garbage.

Other users dispose of the used pouch and its contents in the garbage, which usually necessitates pre-wrapping of the pouch with paper and/or placement of the used pouch in a plastic bag prior to disposal. This is most unsanitary, environmentally unsafe and very embarrassing for the user. Regardless of which measures are taken to dispose of a used ostomy pouch, the process is generally unduly laborious and oftentimes discomforting and most unpleasant.

Ostomates often choose to use what is called a "drainable pouch" whereby the user unclips a clamp at the bottom of a plastic open-ended pouch, squeezing out the contents into the toilet and re-clamping the open end for next usage. These types are supposedly washable and reusable and are a choice for many ostamates for economical reasons.

Thus there is an ongoing effort including numerous attempts to develop an improved ostomy pouch that provides relatively trouble-free flush-ability down a toilet in an environmentally safe and sanitary manner. However, until now there has not been a satisfactory or efficient solution to the problems associated with ostomy bags and their use. The following are some examples of the prior art for references.

A major problem in flushing an ostomy pouch down a toilet is that the coupling or securing structure around the waste inlet opening of the ostomy pouch, such as shown in U.S. Pat. No. 4,372,308, can cause the pouch to become trapped in the flow passages of the toilet or in a connecting pipe or sewer line. Efforts have thus been made to form ostomy pouches of materials that soften and become slimy or slippery when contacted with water to promote flowage in pipelines and flow passages.

While pouches that become slimy or slippery upon contact with water help minimize clogging and trapping problems associated with flush disposal of ostomy pouches, they can be discomforting if they become wet while being worn. Such pouches might discourage a user from engaging in swimming and other physical activity and would require protective covering while showering. Furthermore, such pouches may still cause clogging in toilets with relatively low volume flush capacity.

Another structure that addresses flush disposal of ostomy pouches is taught in U.S. Pat. No. 4,830,187, wherein shown is a carrier sleeve or bag into which a pouch can be placed before flush disposal. The sleeve or bag forms a slimy or slippery layer when exposed to water, thereby sliding on surfaces that might otherwise cause snagging of the pouch. However, since the carrier sleeve conforms to the pouch during flushing, a pouch with a coupling that is not flexible enough to negotiate the flow passages in a toilet may still become trapped even with a slippery carrier sleeve.

Other attempts to resolve the problems associated with ostomy pouches are illustrated within U.S. Pat. Nos. 5,865,819, 5,938,647, 6,723,079, and 5,976,118. Each of these references provides a disposable flushable pouch means. However, one very important disadvantage and drawback inherent within each is the fact that they are still attached to the surrounding area of the stoma of the patient in the typical most inefficient manner. Namely, via an upraised circular protrusion that mates within a circular recess by a friction fit. All of the prior references incorporate this type of attachment means that is very inefficient. Thus, the present invention eliminates this type of attachment means in a new novel manner and which provides most unusual end results as will be seen within the following specification.

OBJECTS AND SUMMARY OF THE INVENTION

It is thus an object of the present invention to provide an ostomy pouch that can be easily flushed down a toilet, even a water-saver toilet, and which has an optimum height, width, and convergence angle to facilitate flush disposal. Furthermore, it is to be constructed from a biodegradable material that will not increase quantity of disposal waste, as it is extremely lightweight, sleek and of little bulk.

Yet another object of the present invention is to provide an ostomy appliance that eliminates the standard attachment means used for attaching the appliance onto the surrounding are of the stoma on the user. The attachment means being very unique as it is not a friction fit which is most advantageous and provides unusual end results heretofore not attained. This is a most important object of the present invention as many patients cannot attach the appliance due to physical disorders or the like, such as arthritis or simply lack of strength, etc. Therefore, the present attachment means is releasable by slightly turning the attachment and this in turn automatically releases the locking mechanism and this is most advantageous and desirable.

Still a further object of the present invention is to provide an ostomy appliance that eliminates or highly reduces actual contact between the user and/or the attendant and the contaminated waste. This is extremely important as the waste maybe extremely dangerous or toxic, not only due to airborne bacteria but also due to diseases such as aids and the like. It is to be understood that because the bag for the contaminated waste is completely biodegradable and flushable, this further eliminates the disadvantages associated within the prior art. For example, current users tend to dispose of the waste via a waste receptacle that in turn is delivered to a disposal truck and then onto a remote disposal site. Thus, the user, the garbage pick-up personnel, and anyone at the disposal site are all exposed to the contaminated waste as well as any air borne bacteria that is also further released.

Another important object of the present invention is to provide an ostomy appliance that is much more user friendly than that of the known prior art. The appliance has been made simpler with improved efficiency and is much more cost effective for production as well as more affordable for the end user. It is to be noted current ostomy pouches are very expensive and thus many users cannot afford proper care. Whereby, a user because of cost will use a pouch again and again even when it has become overly worn and/or unsanitary. Therefore, this is an important problem that the present invention addresses and resolves in a new and novel manner.

Yet another important object of the present invention is to provide an ostomy appliance that eliminates common problems associated within the known prior art. For example, a very typical problem is that the waste tends to get clogged between the stoma discharge area and the pouch opening and thus will not empty properly into the bag. This is most inconvenient and causes numerous difficulties that the present appliance clearly recognizes, addresses, resolves and eliminates in a novel manner. For example, the ostomy appliance is so designed as to be slightly spaced outwardly from the stoma area and this facilitates contaminate flow. Furthermore, the opening within the outer bag is larger than those within the prior art and this allows for easier removal of the inner bag when full from the outer bag.

Still a further object of the present ostomy appliance is to include within the outer bag a charcoal filter system for elimination of odors or the like and may be easily removably replaced. This is also important as this allows the outer bag to be reusable and sanitized if so desired.

Yet another object of the present invention is to provide an ostomy appliance that may further include a protective shield for protecting the appliance and stoma area. This is important as when in use the area tends to be subjected to objects that may interfere. For example, waist belts, safety belts, automobile seat belts, pants and the like tend to interfere with the stoma area and thus a protective shield is desirable. Furthermore, the protective shield is so designed that it will not interfere with function of the appliance as it still allows for open communication between the stoma and pouch in a non-intrusive manner.

Still another object of the present invention is to provide an ostomy appliance that may include a mirror. This is most advantageous for users who cannot easily view the stoma site, such as those users who are overweight, disabled, and/or woman having large breasts, etc. To further resolve this matter the present ostomy appliance includes an optional stoma locator adaptor that allows a user to properly position and align the associated attachment flange against the stoma area of the user in a simplified manner.

Also, a further object of the present invention is to provide an ostomy appliance that may include a unique optional breather flange. It is to be understood in many instances the stoma itself and the surrounding area may become infected and/or irritated due to use of the adhesive on the skin. Thus, it is desirable to provide as an option a breather flange that eliminates use of any adhesive pad and which is usable when the main component of the ostomy appliance is not in use. For example, it is advantageous to allow air to circulate around the stoma area so as to relieve any irritation and/or allow for healing thereof.

Yet another object of the present invention is to provide an ostomy appliance that includes air-circulation holes within the adhesive attached flange associated therewith. This is important, as within all of the prior art the adhesive attached flange is solid having no breather holes. Thus air-circulation holes would be most advantageous and reduce irritation. Furthermore, this allows the user to re-position the adhesive attached flange with the holes in different positions allowing for different areas to be exposed to the air.

Still another object of the present invention is to provide an ostomy appliance that may include finger grips for increased ease of attaching and/or removing the appliance from the body.

Other objects and advantages will be seen when taken into consideration with the following drawings and specification.

BRIEF DESCRIPTION OF THE DRAWINGS

FIG. 1 is a perspective overview for the preferred attachment flange.

FIG. 2 is a perspective overview for the preferred attachment collar having the inner bag affixed thereon.

DETAILED DESCRIPTION OF THE DRAWINGS

Figure 3:
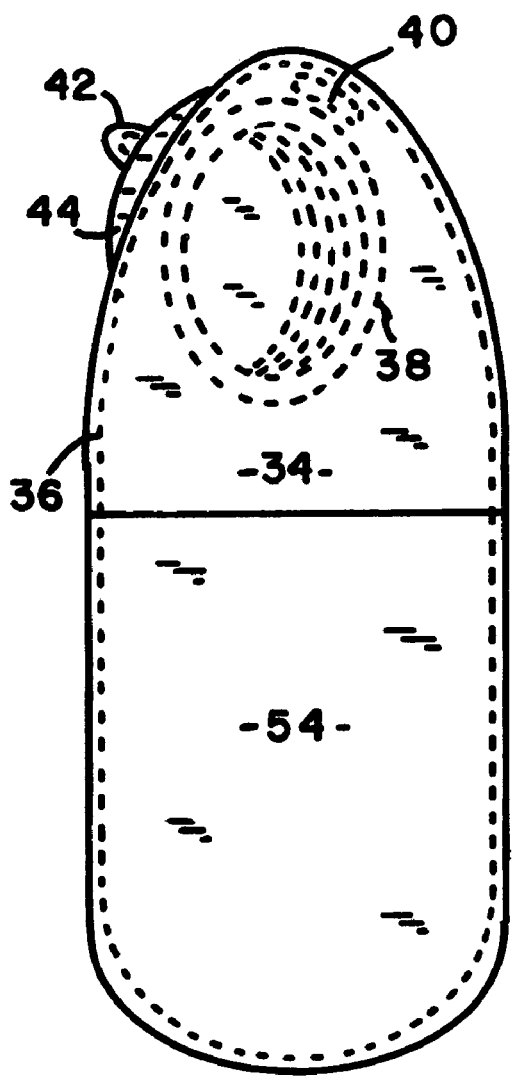
FIG. 3 is perspective overview for the preferred outer bag.
Figure 4:
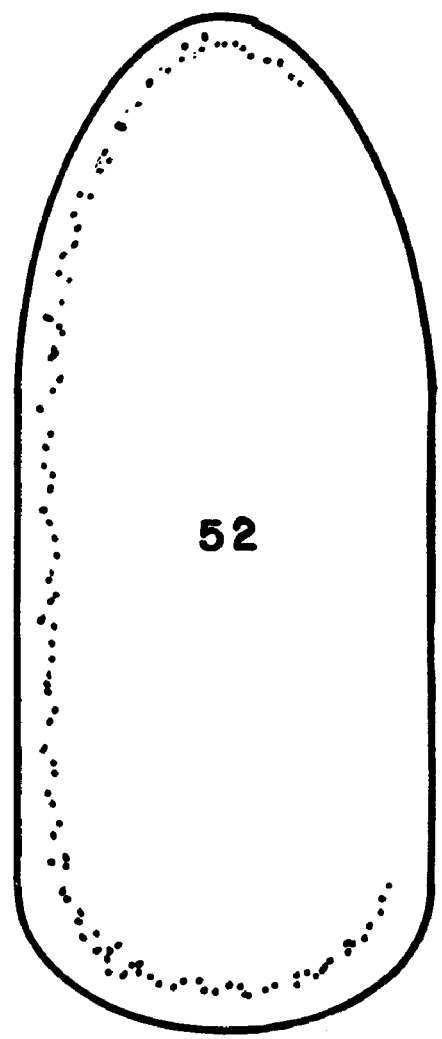
FIG. 4 is a perspective overview for the protective shield.

Referring now in detail to the drawings wherein like characters refer to like elements throughout the various views as follows. Within FIG. 1 the preferred embodiment is depicted for the attachment flange (10). It is to be noted attachment flange (10) can be made from any suitable materials of engineering choice, thus the materials as herein described are only exemplary and thus the invention is not to be limited thereto.

Attachment flange (10) substantially comprising in combination an attachment pad (12), a body gasket (13), an externally threaded outwardly extending circular protrusion (14) and an internal elongated outwardly extending protrusion (16). Whereby the attachment pad (12), body gasket (13), externally threaded outwardly extending circular protrusion (14) and internal elongated outwardly extending protrusion (16) are interconnected and in combination form the attachment flange (10). Thus, it is to be noted each of the components of the attachment flange (10) may be integrally formed such as by a plastic mold injection or the like.

As can be seen within FIG. 1, the preferred embodiment may further include an optional feature for added efficiency wherein attachment pad (12) includes at least one elastic inlay (18) which is most advantageous as this allows for increased comfort due to enhanced flexing of the attachment flange (10) attributable to the elastic inlay (18). Thus the attachment pad (12) is much more user friendly as it tends to adjust or flex more readily with the users body movements. It is to be understood the elastic inlay may be independent elastic strips located at various positions therein or it may be a continuous strip, a combination of strips, or the like depending on engineering and/or end user preferences.

Attachment flange (10) having attachment means for removably attaching attachment pad (12) onto the stoma area of a user. It is to be noted any suitable type of attachment means may be used depending on engineering and/or end user preferences. However, a most functional attachment means includes a peel-a-way removable adhesive strip (20) that is adhesively attached onto attachment pad (12). Whereby, upon removal of the adhesive strip (20) an adhesive residue is deposited upon attachment pad (12) and the adhesive residue allows attachment pad (12) to be removably adhered yet securely affixed onto the stoma area of the user. It is to be noted that only a partial amount of adhesive may remain or the entire pad may be completely covered depending on engineering or end user preferences.

Attachment flange (10) further having attachment means for removably attaching an outer bag (34) thereon with the attachment means and the outer bag being described later herein.

Attachment pad (12) may further include at least one finger grip (22) which when grasped by the user will aid them in removal of attachment pad (12). However, it is contended at least two opposed finger grips may be more convenient as this allows for more evenly distributed pressure release.

Attachment flange (10) further having attachment means for removably attaching a coupling member (24) thereon. It is to be understood many different types of attachment means may be incorporated, thus the following is only exemplary of one possible embodiment. The noted attachment means substantially comprising the internal elongated outwardly extending protrusion (16) having first and second outwardly extending pins (26) that are opposed to each other respectively and the circular coupling member (24) having first and second angular receiving slots (28) opposed to each other respectively. Whereby, circular coupling member (24) may be easily attached onto internal elongated outwardly extending protrusion (16) by positioning first and second outwardly extending pins (26) within corresponding first and second angular receiving slots (28) and then slightly manually turning until stopped. Thus locking and firmly attaching internal elongated outwardly extending protrusion (16) onto circular coupling member (24), in an affixed yet removable manner.

It is to be noted circular coupling member (24) is made from a biodegradable material of engineering choice, such as very thin paper or the like. Circular coupling member (24) having attachment means for attaching biodegradable inner bag (30) thereon. For example one suitable attachment means includes an internal circular surface area and an external circular surface area that allow for removable attachment of biodegradable inner bag (30) thereon. The biodegradable inner bag (30) being substantially elongated having one open end and made from any suitable flexible material. Whereby, the open end may be inserted inside and throughout circular coupling member (24) and then folded over the external circular surface area in a manner that completely surrounds the internal and external circular surface areas and thus captures circular coupling member (24) therein, as clearly depicted in FIG. 2. However, if preferred inner bag (30) and coupling member (24) may be formed as one unit and thus inserting and folding of the inner bag is eliminated. It is to be noted for improved function, it may be advantageous to further include air-ventilation holes (32) that allow ventilation for biodegradable inner bag (30) and which may be either formed within the open end or as herein depicted formed within circular coupling member (24).

With further reference to FIG. 2 and to the biodegradable inner bag (30) it is to be noted any suitable biodegradable or dissolvable material of engineering choice may be used. For example, there are numerous materials that are biodegradable including a type of polymer base. Whereby, flush ability is achieved by forming the inner bag from a film material having load-bearing properties that provides a relatively strong and tough inner bag when dry but when subjected to water such as within a toilet bowl becomes limp, soft and/or slippery and dissolves or disintegrates, or at least degrades when disposed of within the toilet bowl water. Therefore suitable materials of choice may include but are limited to polyvinyl alcohol, poly (alkylene oxide), hydroxyethyl cellulose, hydroxypropyl cellulose, polyvinyl pyrrolidone, polyacrylamide, polyacrylic acid, or poly (vinyl methyl ether-co-maleic anhydride), or the like.

As an alternative and or in combination, biodegradable inner bag (30) may further include additional means for causing the bag to further disintegrate when disposed of within a toilet. For example, as further depicted within FIG. 2, inner bag (30) provides a sealed compartment (46) for containment of a substance that may be in the form of a capsule or tablet (48). It is to be noted any suitable type of substance that aids in dissolving may be used depending on engineering choice. However, some suitable dissolving means include either an alkali additive or exothermic reagent or the like but the invention is not to be limited thereto.

For increased ease of use, sealed compartment (46) also provides a rip chord (50) which when pulled automatically opens the compartment (46) and exposes tablet (48). Whereby, when the inner bag (30) with circular coupling member (24) and tablet (48) are disposed of within a toilet bowl, each completely dissolves in an environmentally friendly manner.

Referring now to FIG. 3 wherein the outer bag (34) is depicted substantially comprising of a flexible body which forms an internal compartment (36) and which is in open communication with an internally threaded circular attachment flange (38) that is fixedly attached thereon and/or integrally formed therewith. Whereby, it can be seen that internally threaded circular attachment flange (38) and externally threaded outwardly extending circular protrusion (14) may be removably attached together by threadably engaging internally threaded circular attachment flange (38) into outwardly extending circular protrusion (14).

It is to be understood that outer bag (34) is of a shape and size to easily removably receive biodegradable inner bag (30) therein, and when the inner bag (30) is full it may be easily retrieved from within outer bag (34) via the enlarged opening within internally threaded circular attachment flange (38). Thus, internally threaded circular attachment flange (38) is large enough in circumference so as to allow the inner bag (30) to be easily slidably removed there through and throughout in a convenient manner.

For increased function, outer bag (34) may also include a filter means (40) for filtering and/or removing any undesirable odors that may emanate from the biodegradable inner bag (30). Furthermore, it is preferred for convenience and cost efficiency that the filter means (40) be of the removable and/or replaceable type. It is to be noted that there are numerous types of replaceable filters available in today's market, thus the invention is not to be limited to any specific type, shape or size.

As can be seen in FIG. 3, internally threaded circular attachment flange (38) also provides an outwardly protruding neck portion (44) that functions to distally position the outer bag (34) at the preferred location outwardly from the stoma area of the user. Therefore any waste existing from within the stoma area is allowed to flow outwardly there from and into the inner bag (30) in a non-restricted manner. This is extremely important, as the current ostomy bags tend to continuously clog and this defeats the entire purpose and discourages use. Furthermore, this can be most frustrating and embarrassing. Still further for increased and un-obstructed waste flow, the shape and size of the circular coupling member (24) is important and the preferred embodiment is depicted in FIG. 2. Wherein, circular coupling member (24) provides a first edge and a second edge with the second edge being opposite of slots (28) and most importantly the second edge is cut at an angle. Thus, waste existing there through and outwardly there from is allowed to flow more freely due to this angular shape and of course gravitational influences further assist.

For further convenience and improved function, outer bag (34) may also include at least one thumb/finger grip (42) that aids removal and also provides increased leverage when attaching and/or removing outer bag (34).

Outer bag (34) may include another option if so desired such as a protective shield (52) for protecting the appliance and stoma area. This is important as when in use the area tends to be subjected to objects that may interfere. For example, waist belts, safety belts, pants and the like tend to interfere with the stoma area and thus a protective shield is desirable and most useful. Furthermore, the protective shield is so designed that it will not interfere with function of the appliance as it still allows for open communication between the stoma and pouch in a non-intrusive manner. Another feature unique to the present invention is to include a storage compartment (54) upon outer bag (34) that is of a shape and size to removably receive protective shield (52) therein when not in use.

Figure 5:
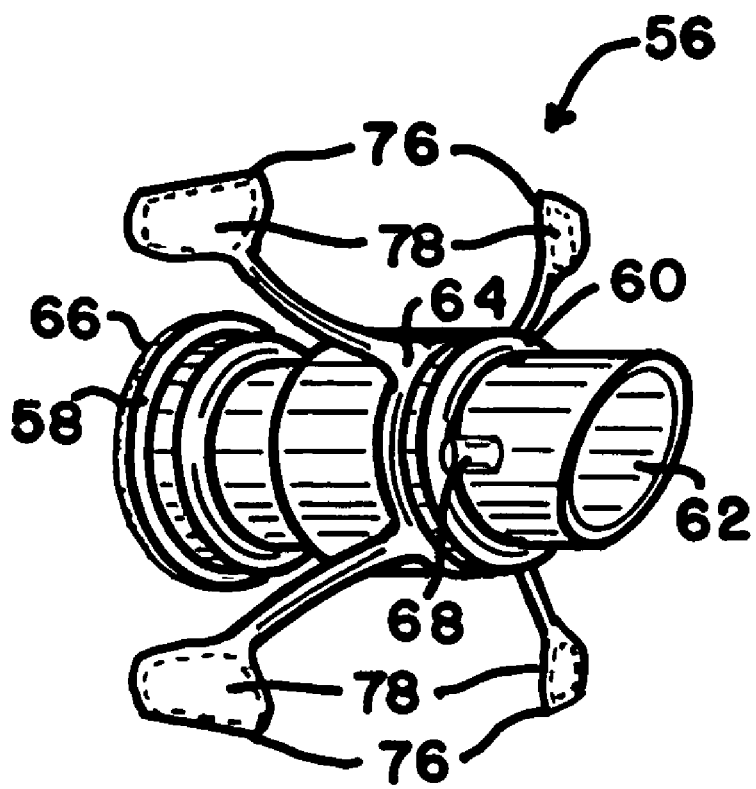
FIG. 5 is a perspective overview for the optional breather flange.

Referring now to FIG. 5 wherein depicted is an alternative breather attachment flange (56). As previously noted many patients are allergic to adhesive and/or over a period of time the adhesive residue tends to irritate the stoma area and/or cause infection. Therefore as an alternative to use of the attachment flange (10) the present invention provides alternative breather attachment flange (56). This is a very important feature of the present invention as nowhere in the prior art do they provide any type of attachment flange that allows the skin surrounding the stoma area to breath which in turn allows time for healing.

It is to be noted the alternative breather attachment flange (56) may be worn either temporarily or permanently depending on the needs of the user. Alternative breather attachment flange (56) substantially comprising of an attachment ring (58), an outwardly extending tubular member (60), body attachment means (64) and bag attachment means (62). Again it is to be understood alternative breather attachment flange (56) can be made from any suitable materials of choice. However, in the preferred embodiment attachment ring (58) and outwardly extending tubular member (60) are each preferably made from a non-rigid material such as flexible soft rubber or the like. This is not only for comfort but also improves function as this allows the alternative breather attachment flange (56) to flex or compress respectively when subjected to any pressure exerted thereon while being worn. Thus reducing stress on the device and providing more comfort for the user. It is to be further understood that body attachment means (64) can again be any suitable attachment means of engineering choice. Thus, the attachment means as depicted herein is only exemplary, as many different suitable types exist. For example, as taught herein one suitable body attachment means (56) is formed from a circular member (64) having flexible outwardly protruding leg extensions (76). The circular member (64) is of a shape and size to be slidably engaged onto alternative breather attachment flange (56) and the leg extensions (76) include adhesive pads (78) (shown in ghost lines) which when removed leave an adhesive residue. Whereby, the leg extensions (76) can be easily positioned and attached onto a location of user choice via the adhesive residue. Yet another option is to include a different type of protective shield (not shown) that is similar to shield (52) and which when positioned over alternative breather attachment flange (56) not only provides protection but also includes leg extensions that have removable adhesive pads that leave a adhesive residue when removed for attaching and also serve to slightly elevate the protective shield so as to be non-intrusive to function of the alternative breather attachment flange (56).

Attachment ring (58) of alternative breather attachment flange (56) is of a shape and size to substantially mate with the stoma orifice of the user and is attachable thereto via an adhesive pad (66). Whereby, when the adhesive pad is removed a residue remains thereon and allows the user to attach alternative breather attachment flange (56) onto the stoma orifice. Attachment ring (58) and bag attachment means (62) being interconnected via outwardly extending tubular member (60) and each may be formed independently or integrally formed from one mold depending on engineering choice.

It is to be understood that bag attachment means (62) is substantially identical to that associated with attachment flange (10). Thus, bag attachment means (62) includes first and second outwardly extending pins (68) (only one shown for clarity purposes) that are opposed to each other respectively and the circular coupling member (24) having first and second angular receiving slots (28) opposed to each other respectively. Whereby, circular coupling member (24) may be easily attached onto bag attachment means (62) by positioning first and second outwardly extending pins (68) within corresponding first and second angular receiving slots (28) and then slightly manually turning until stopped. Thus locking and firmly attaching bag attachment means (62) onto circular coupling member (24), in an affixed yet removable manner.

Figure 6:
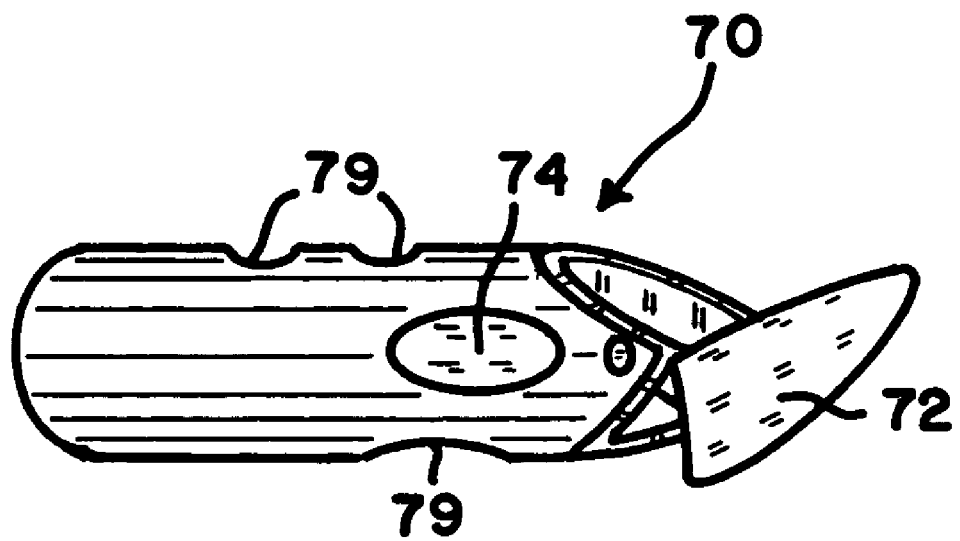
FIG. 6 is a perspective overview for the optional stoma locator adaptor.

Referring now to FIG. 6, wherein depicted is yet another optional feature of the present invention. Namely, a stoma locator adaptor (70) that serves to aid a user to properly align and position attachment flange (10) onto the stoma orifice of the user. This is a very important feature as nowhere in the known prior art do address, suggest or even imply such a novel device. This is especially useful for users who cannot easily view the stoma orifice such as those having large breasts and/or large stomachs or the like and this is a very common problem. Therefore, the stoma locator adaptor (70) provides alignment means in the form of an elongated tube having a first end and a second end. The first end being substantially of a shape and size to having a flush mating relationship with the stoma orifice of the user. The second end of the stoma locator adaptor (70) providing viewing means such as in the form of a mirror (72) that is adjustable between various positions of user choice. Also, it may be advantageous if the elongated tube is formed ergonomically so as to be very user friendly, thus finger and/or thumb indents (79) may be most useful. Furthermore if so desired, the elongated tube may also include a push-button battery activated light means (74) for illuminating the interior of the elongated tube to further aid visualizing and proper aligning.

Whereby, it can be seen that when a user wishes to attach the attachment flange (10) onto the stoma orifice, the user simply turns on the light if included, grasps the stoma locator adaptor (70) preferably in a comfortable manner using the finger and/or thumb indents (79), positions the mirror, and gently while viewing through the mirror aligns the stoma locator adaptor (70) into position against the stoma orifice, slidably engages the attachment flange (10) over stoma locator adaptor (70) until proper alignment is achieved, attaches the attachment flange (10) in the usual manner and then removes the stoma locator adaptor (70). It is to be understood this is very functional as the stoma orifice is very visible there thru as the stoma orifice has a natural pinkish or red color that is identifiable from the surrounding tissue and is thus easily seen via the mirror and push-button battery activated light means (74).

It can now be seen herein taught is a novel improved ostomy appliance that is user-friendly, sanitary, environmentally safe, and further includes novel improved attachment means. Additionally, the appliance provides optional features including a temporary breather flange that allows for healing of the stoma orifice when irritated or infected and a novel stoma locator adaptor that aids a user and provides proper placement and alignment of the appliance in a manner heretofore not taught.

It can now be seen and further understood that the ostomy appliance of the present invention may be produced as a kit having different combinations of components therein depending on engineering choice or end user preferences, or if preferred each of the components may be sold independently.

It is to be noted and understood although the invention has been directed or specifically designed for use as an ostomy appliance, other uses are inherent such as a urinary incontinence pouch or the like and is thus not limited in use thereto.

Although the invention has been herein shown and described in what is conceived to be the most practical and preferred embodiment, it is recognized that departures may be made there from within the scope and spirit of the invention, which is not to be limited to the details disclosed herein but is to be accorded the full scope of the claims so as to embrace any and all equivalent devices and apparatuses.

The invention claimed is:

1. An ostomy appliance comprising: an attachment flange; a coupling member; a biodegradable inner bag; and an outer bag; said attachment flange being formed from an attachment pad, a body gasket, an externally threaded outwardly extending circular protrusion and an internal elongated outwardly extending protrusion each of which are interconnected in combination, said attachment flange having attachment means for removably attaching said coupling member thereon, said attachment flange having attachment means for removably attaching said outer bag thereon, said attachment flange having attachment means for removably attaching said attachment pad onto a stoma orifice of a user, said coupling member having attachment means for attaching said biodegradable inner bag thereon, said outer bag being of a shape and size to easily removably receive said biodegradable inner bag therein, said attachment flange having attachment means for removably attaching said coupling member thereon comprising: said internal elongated outwardly extending protrusion having first and second outwardly extending pins that are opposed to each other and said circular coupling member having first and second angular receiving slots that are opposed to each other, whereby;

said circular coupling member is configured to easily attached onto said internal elongated outwardly extending protrusion by positioning said first and said second outwardly extending pins within corresponding said first and said second angular receiving slots and when manually slightly turned until stopped locks and firmly attaches said internal elongated outwardly extending protrusion onto said circular coupling member in an affixed yet removable manner.

2. The ostomy appliance of claim 1 wherein said attachment flange having attachment means for removably attaching said outer bag thereon comprising: said outer bag having an internally threaded circular attachment flange fixedly attached thereon, said internally threaded circular attachment flange and said externally threaded outwardly extending circular protrusion may be removably attached together by threadably engaging said internally threaded circular attachment flange into said outwardly extending circular protrusion.

3. The ostomy appliance of claim 1 wherein said attachment flange having attachment means for removably attaching said attachment pad onto a stoma orifice of a user comprising: a peel-a-way adhesive strip that is adhesively attached onto said attachment pad, whereby;

upon removal of said peel-a-way adhesive strip, an adhesive residue is deposited upon said attachment pad and said adhesive residue allows said attachment pad to be removably adhered yet securely affixed onto said stoma orifice of said user.

4. The ostomy appliance of claim 1 wherein said coupling member having attachment means for attaching said biodegradable inner bag thereon comprising: said coupling member having an internal circular surface area and an external circular surface area and said biodegradable inner bag being elongated having one open end, whereby;

said open end may be inserted inside and throughout said circular coupling member then folded over said external circular surface area in a manner that completely surrounds said internal and said external circular surface areas and thus captures said circular coupling member therein.

5. The ostomy appliance of claim 1 wherein said attachment pad further includes at least one elastic inlay, whereby:

said at least one elastic inlay provides increased comfort due to enhanced flexing of said attachment flange attributable to said at least one elastic inlay.

6. The ostomy appliance of claim 1 wherein said attachment pad further includes at least one finger grip.

7. The ostomy appliance of claim 1 wherein said coupling member is made from a biodegradable material.

8. The ostomy appliance of claim 1 wherein said outer bag further includes a storage compartment that is of a shape and size to receive a protective shield therein.

9. The ostomy appliance of claim 1 wherein said outer bag further includes at least one thumb/finger grip.

10. The ostomy appliance of claim 1 wherein said outer bag further includes a filter means.

11. The ostomy appliance of claim 10 wherein said filter means is replaceable.

12. The ostomy appliance of claim 1 further includes an alternative breather attachment flange that is used as an alterative to said attachment flange.

13. The ostomy appliance of claim 12 wherein said alternative breather attachment flange comprising: an attachment ring; an outwardly extending tubular member; body attachment means; and bag attachment means.

14. An ostomy appliance comprising: an attachment flange; a coupling member; a biodegradable inner bag; and an outer bag; said attachment flange being formed from an attachment pad, a body gasket, an externally threaded outwardly extending circular protrusion and an internal elongated outwardly extending protrusion each of which are interconnected in combination, said attachment flange having attachment means for removably attaching said counting member thereon, said attachment flange having attachment means for removably attaching said outer bag thereon, said attachment flange having attachment means for removably attaching said attachment pad onto a stoma orifice of a user, said coupling member having attachment means for attaching said biodegradable inner bag thereon and said outer bag being of a shape and size to easily removably receive said biodegradable inner baa therein and said coupling member further includes air ventilation holes.

15. An ostomy appliance comprising: an attachment flange; a coupling member; a biodegradable inner bag; and an outer bag; said attachment flange being formed from an attachment pad, a body gasket, an externally threaded outwardly extending circular protrusion and an internal elongated outwardly extending protrusion each of which are interconnected in combination, said attachment flange having attachment means for removably attaching said coupling member thereon, said attachment flange having attachment means for removably attaching said outer bag thereon, said attachment flange having attachment means for removably attaching said attachment pad onto a stoma orifice of a user, said coupling member having attachment means for attaching said biodegradable inner bag thereon and said outer bag being of a shape and size to easily removably receive said biodegradable inner bag therein and a stoma locator adaptor that serves to aid said user to properly align and position said attachment flange onto said stoma orifice of said user, said stoma locator adaptor comprising: an elongated tube having a first end and a second end, said first end being of a shape and size to have a flush mating relationship with said stoma orifice of said user and said second end providing viewing means.

16. The ostomy appliance of claim 15 wherein said viewing means is in the form of a mirror.

17. The ostomy appliance of claim 16 wherein said mirror is adjustable between various positions of choice.

18. The ostomy appliance of claim 15 wherein said elongated tube is ergonomically designed including finger and/or thumb indents.

19. The ostomy appliance of claim 15 wherein said elongated tube further includes a push-button battery activated light means.

* * * * *